(12) United States Patent
Holzgrefe

(10) Patent No.: US 6,743,181 B2
(45) Date of Patent: Jun. 1, 2004

(54) SYSTEM AND METHOD FOR MEASURING VENTRICULAR FUNCTION

(75) Inventor: Henry H. Holzgrefe, Fayetteville, NY (US)

(73) Assignee: Bristol-Myers Squibb Co., Princeton, NJ (US)

( * ) Notice: Subject to any disclaimer, the term of this patent is extended or adjusted under 35 U.S.C. 154(b) by 38 days.

(21) Appl. No.: 10/209,727

(22) Filed: Aug. 1, 2002

(65) Prior Publication Data

US 2003/0036707 A1 Feb. 20, 2003

Related U.S. Application Data

(60) Provisional application No. 60/309,640, filed on Aug. 2, 2001.

(51) Int. Cl.[7] ............................. A61B 5/02; A61M 29/00
(52) U.S. Cl. ................... 600/508; 600/481; 604/96.01; 604/97.01; 604/99.04
(58) Field of Search ............................... 600/508, 526, 600/481, 483, 485, 486, 300, 301; 604/96.01, 97.01, 99.04, 99.02

(56) References Cited

U.S. PATENT DOCUMENTS

| | | | | |
|---|---|---|---|---|
| 4,116,589 A | * | 9/1978 | Rishton | 417/384 |
| 6,241,706 B1 | * | 6/2001 | Leschinsky et al. | 604/99.01 |
| 6,245,008 B1 | * | 6/2001 | Leschinsky et al. | 600/18 |

OTHER PUBLICATIONS

Alanen, K. et al., "Ischaemic Contracture and Myocardial Perfusion in Isolated Rat Heart", Virchows Arch. A Path. Anat. and Histol., vol. 385, pp. 143–149 (1980).

Alanen, K.A. et al., "Effect of verapamil on reperfusion damage and calcium paradox in isolated rat heart", Exp. Path., vol. 25, pp. 131–138 (1984).

Berrebi–Bertrand, I. et al., "Inotropic effect of ouabain in hypertrophied rat heart", Pflügers Arch., European Journal of Physiology, vol. 417, pp, 247–254 (1990).

Brooks, W.W. et al., "Oxygen Cost of Stress Development in Hypertropheid and Failing Hearts From the Spontaneously Hypertensive Rat", Hypertension, vol. 21, No. 1, pp. 56–64 (1993)

Cave, A.C. et al., "ATP Synthesis During Low–Flow Ischemia: Influence of Increased Glycolytic Substrate", Circulation, vol. 101, pp. 2090–2096 (2000).

Chevalier, B. et al., "Diminished toxicity of ouabain in the hypertrophied rat heart", Pflügers Arch., European Journal of Physiology, vol. 414, pp. 311–316 (1989).

Chevalier, B. et al., "Screening of Inotropic Drugs on Isolated Rat and Guinea Pig Hearts", Journal of Pharmacological Methods, vol. 17, pp. 313–326 (1987).

(List continued on next page.)

*Primary Examiner*—Max F. Hindenburg
*Assistant Examiner*—Navin Natnithithadha
(74) *Attorney, Agent, or Firm*—Stephen B. Davis

(57) ABSTRACT

A system and method for measuring ventricular function in an isolated, perfused heart using an intraventricular balloon connected to a plumbing circuit containing a fluid, the plumbing circuit including (a) a valve for selectively opening the plumbing circuit to (i) atmospheric pressure or (ii) a pressure control circuit of a pressure control apparatus or (b) a pressure control apparatus which can be selectively connected to the plumbing circuit, including the steps of establishing a base pressure by (1) opening the valve to atmospheric pressure or the pressure control circuit or (2) operating the pressure control apparatus, after equalization of the pressure within the intraventricular balloon with the base pressure, closing the valve or stopping operation of the pressure control apparatus, following the closing of the valve, measuring ventricular function as a function of a titrated infusion of fluid into the plumbing circuit and intraventricular balloon, performing an intervention, and repeating at least the first three steps.

17 Claims, 2 Drawing Sheets

OTHER PUBLICATIONS

Daniels, M. et al., "Velocity of Sarcomere Shortening in Rat Cardiac Muscle: Relationship to Force, Sarcomere Length, Calcium and Time", J. Physiol., vol. 355, pp, 367–381 (1984).

Docherty, J.C. et al., "An inhibitor of poly (ADP–ribose) synthetase activity reduces contractile dysfunction and preserves high energy phosphate levels during reperfusion of the ischaemic rat heart", British Journal of Pharmacology, vol. 127, pp. 1518–1524 (1999).

Döring, H.J., "The Isolated Perfused Heart According to Langendorff Technique—Function—Application", Physiologie Bohemoslovaca, vol. 39, pp. 481–504 (1990).

Eberli, F.R. et al., "Exacerbation of Left Ventricular Ischemic Diastolic Dysfunction by Pressue–Overload Hypertrophy: Modification by Specific Inhibition of Cardiac Angiotensin Converting Enzyme", Circulation Research, vol. 70, No. 5, pp. 931–943 (1992).

Falsetti, H.L. et al., "Analysis and Correction of Pressure Wave Distortion in Fluid–Filled Catheter Systems", Circulation, vol. 49, pp. 165–172 (1974).

Gao, F. et al., "Mechanism of decreased adenosine protection in reperfusion injury of aging rats", Am. J. Physiol. Heart Circ. Physiol., vol. 279, pp. H329–H338 (2000).

Glantz, S.A. et al., "Determination of frequency response from step response: application to fluid–filled catheters", American Journal of Physiology, vol. 236, pp. H376–H378 (1979).

Grover, G.J. et al., "Glyburide–reversible cardioprotective effect of BMS–180448 is independent of action potential shortening", Cardiovascular Research, vol. 30, pp. 731–738 (1995).

Grover, G.J. et al., "Glyburide–Reversible Cardioprotective Effects of BMS–180448: Functional and Energetic Considerations", Journal of Cardiovascular Pharmacology, vol. 29, pp. 28–38 (1997).

Guppy, L.J. et al., "Effect of Calcium, Bay K 8644, and Reduced Perfusion on Basic Indices of Myocardial Function in Isolated Hearts from Rats After Prolonged Exposure to Ethanol", Journal of Cardiovascular Pharmacology, vol. 34, pp. 480–487 (1999).

Harding, S.E. et al., "Contractile Responses of Isolated Adult Rat and Rabbit Cardiac Myocytes to Isoproterenol and Calcium", J. Mol. Cell Cardiol., vol. 20, pp. 635–647 (1988).

Hata, Y. et al., "Linear $O_2$ Use—Pressure–Volume Area Relation from Curved End–Systolic Pressure—Volume Relation of the Blood–Perfused Rat Left Ventricle", Japanese Journal of Physiology, vol. 48, pp. 197–204 (1998).

Humphrey, S.M. et al., "The Effect of an Isovolumic Left Ventricle on the Coronary Vascular Competence during Reflow after Global Ischemia in the Rat Heart", Circulation Research, vol. 49, No. 3, pp. 784–791 (1981).

Humphrey, S.M. et al., "The Influence of the No–Reflow Phenomenon on Reperfusion and Reoxygenation Damage and Enzyme Release from Anoxic and Ischaemic Isolated Rat Hearts", J. Mol. Cell Cardiol., vol. 16, pp. 915–930 (1984).

Inagaki, K. et al., "Anti–Ischemic Effect of a Novel Cardioprotective Agent, JTV519, Is Mediated Through Specific Activation of δ–Isoform of Protein Kinase C in Rat Ventricular Myocardium", Circulation, vol. 101, pp. 797–804 (2000).

Inarejo, M. et al., "Effects of Catecholamine Uptake Inhibitors on the Positive Inotropic Responses to Isoprenaline, Dobutamine and Dopexamine in Human, Rat and Guinea–Pig Atrial Heart Muscle", Arch. int. Pharmacodyn., vol. 323, pp. 50–61 (1993).

Inserte, J. et al., "Urodilatin limits acute reperfusion injury in the isolated rat heart", Cardiovascular Research, vol. 45, pp. 351–359 (2000).

Jiang, M.T. et al., "Age–Related Alterations in the Phosphorylation of Sarcoplasmic Reticulum and Myofibrillar Proteins and Diminished Contractile Response to Isoproterenol in Intact Rat Ventricle", Circulation Research, vol. 72, No. 1, pp. 102–111 (1993).

Kass, D.A. et al., "From 'Emax' to pressure–volume relations: a broader view", Circulation, vol. 77, No. 6, pp. 1203–1212 (1988).

Kusumoto, F.M. et al., "Responses to Calcium and Binding of $^3$H–Nimodipine in the Atrioventricular Node, Atria, and Ventricles of Mature and Old Male Fischer 344 Rats", Journal of Cardiovascular Pharmacology, vol. 26, pp. 348–353 (1995).

Langendorff, O., "Untersuchungen am überlebenden Säugethierherzen", Pflugers Archives ges. Physiology, pp. 291–331 (1895).

Lee, S. et al., "Effects of Myosin Isozyme Shift on Curvilinearity of the Left Ventricular End–Systolic Pressure–Volume Relation of In Situ Rat Hearts", Japanese Journal of Physiology, vol. 48, pp. 445–455 (1998).

Lelievre, L.G. et al., "Effects of calcium on the heterogeneity of the $Na^+$, $K^+$–ATPase forms in rat heart", Basic Research in Cardiology, vol. 79 Supp., pp. 128–133 (1984).

Lelievre, L.G. et al., "Prolonged responsiveness to ouabain in hypertrophied rat heart: physiological and biochemical evidence", American Journal of Physiology, vol. 250, pp. H923–H931 (1986).

Lelievre, L.G. et al., "Respective Involvements of High– and Low–Affinity Digitalis Receptors in the Inotropic Response of Isolated Rat Heart to Ouabain", Biochemical Pharmacology, vol. 35, No. 20, pp. 3449–3455 (1986).

Lipasti, J.A. et al., "Ischaemic contracture in isolated rat heart: reversible or irreversible myocardial injury?" Exp. Path., vol. 28, pp. 89–95 (1985).

Lipasti, J.A. et al., "The relationship between ischemic contracture and no–reflow phenomenon in isolated rat heart", Basic Res. Cardiol., vol. 77, pp. 404–410 (1982).

Mirsky, I., "Assessment of diastolic function: suggested methods and future considerations", Circulation, vol. 69, No. 4, pp. 836–841 (1984).

Mirsky, I. et al., "The Contractile State as the Major Determinant in the Evolution of Left Ventricular Dysfunction in the Spontaneously Hypertensive Rat", Circulation Research, vol. 53, No. 6, pp. 767–778 (1983).

Osada, M. et al., "Ischemic preconditioning prevents I/R–induced alterations in SR calcium–calmodulin protein kinase II", Am. J. Physiol. Heart Circ. Physiol. vol. 278, pp. H1791–H1798 (2000).

Paradise, N.F. et al., "Left ventricular function of the isolated, genetically obese rat's heart", American Journal of Physiology, vol. 248, pp. H438–H444 (1985).

Sagawa, K., "The End–systolic Pressure–Volume Relation of the Ventricle: Definition, Modifications and Clinical Use", Circulation, vol. 63, No. 6, pp. 1223–1227 (1981).

Sagawa, K., "The Ventricular Pressure–Volume Diagram Revisited", Circulation Research, vol. 43, No. 5, pp. 677–687 (1978).

Sato, T. et al., "ESPVR of in situ rat left ventricle shows contractility–dependent curvilinearity", American Journal of Physiology, vol. 274, pp. H1429–H1434 (1998).

Schlant, R.C., "Normal Physiology of the Cardiovascular System", The Heart, 4th ed., McGraw–Hill, New York, Hurst, J.W. ed., pp. 71–100 (1978).

Stefanon, I. et al., "Left ventricular length dependent activation in the isovolumetric rat heart", Cardiovascular Research, vol. 24, pp. 254–256 (1990).

Stefanon, I. et al., "The Relationship Between Extracellular Calcium and Isovolumic Systolic Pressure in the Langendorff–Perfused Rat Heart", Brazilian J. Med. Biol. Res., vol. 22, pp. 905–907 (1989).

Strömer, H. et al., "Exogenously Administered Growth Hormone and Insulin–like Growth Factor–I Alter Intracellular $Ca^{2+}$ Handling and Enhance Cardiac Performance: In Vitro Evaluation in the Isolated Isovolumic Buffer–Perfused Rat Heart", Circ. Res., vol. 79, No. 2, pp. 227–236 (1996).

Strömer, H. et al., "$Na^+/H^+$ Exchange Inhibition With HOE642 Improves Postischemic Recovery due to Attenuation of $Ca^{2+}$ Overload and Prolonged Acidosis on Reperfusion", Circulation, vol. 101, pp. 2749–2755 (2000).

Strömer, H. et al., "Validation of different methods to compare isovolumic cardiac function in isolated hearts of varying sizes", American Journal of Physiology, vol. 272, pp. H501–H510 (1997).

Szabó, G. et al., "Effects of Nitric Oxide Synthesis on Reperfusion Injury and Catecholamine Responsiveness in a Heterotopic Rat Heart–Transplantation Model", Journal of Cardiovascular Pharmacology, vol. 31, pp. 221–230 (1998).

Tsujimoto, G. et al. "A unique pressor response to isoprenaline in the pithed rat during triiodo–L–thyronine($T_3$)–induced hyperthyroidism", Naunyn–Schmiedeberg's Arch. Pharmacol., vol. 334, pp. 138–144 (1986).

Vassallo, D.V. et al., "Effects of Isoproterenol on the Mechanical Activity of Isolated Papillary Muscles and Perfused Rat Hearts in Various Calcium Concentrations", Pharmacological Research, vol. 29, No. 3, pp. 251–260 (1994).

Wannenburg, T. et al., "End–systolic pressure–volume and $MV_{O_2}$–pressure–volume area relations of isolated rat hearts", American Journal of Physiology, vol. 262, pp. H1287–H1293 (1992).

Watts, J.A. et al., "Trace Amounts of Albumin Protect Against Ischemia and Reperfusion Injury in Isolated Rat Hearts", J. Mol. Cell Cardiol., vol. 31, pp. 1653–1662 (1999).

Wheatley, A.M. et al., "The Effect of External Calcium Concentration on the Negative Inotropic Action of Dantrolene in Isolated Hyperthyroid and Euthyroid Heart", Pharmacological Research, vol. 24, No. 1, pp. 65–74 (1991).

Woo, N.D. et al., "Neuropeptide Y Prevents Agonist–Stimulated Increases in Contractility", Hypertension, vol. 26, No. 3, pp. 480–484 (1995).

Xiao, X.–H. et al., "Role of $Na^+/H^+$ Exchanger During Ischemia and Preconditioning in the Isolated Rat Heart", Circulation Research, vol. 85, pp. 723–730 (1999).

* cited by examiner

SYSTEM AND METHOD FOR MEASURING VENTRICULAR FUNCTION

CROSS-REFERENCE TO RELATED APPLICATIONS

This application claims priority from U.S. Serial No. 60/309,640 filed Aug. 2, 2001.

BACKGROUND OF THE INVENTION

The present invention relates to measuring ventricular function.

Ventricular function is often measured by researchers in an isolated heart, such as an isolated rat heart. The use of an isolated heart allows a broad spectrum of biochemical, physiological, morphological, and pharmacological indices to be measured without the presence of confounding effects of other organs, the systemic circulation, and peripheral complications. One method that researchers often use is the Langendorff method. In the Langendorff method, a balloon attached to a cannula is inserted into the heart and attached to a reservoir containing oxygenated perfusion fluid. The fluid is delivered down the aorta in a retrograde direction at either a constant flow rate or at a constant hydrostatic pressure. The aortic valves are forced shut and the perfusion fluid is directed into the coronary ostia, perfusing the entire ventricular mass of the heart and draining into the right atrium via the coronary sinus.

Although the size of an isolated heart changes under many conditions, such as with ischemia, reperfusion, or drug treatment, in the traditional Langendorff method, any changes in the size of the heart are not taken into account. The result is the incorporation of a systematic error into repeated measurements of ventricular function following interventions. The present invention takes the changing size of the heart into account in calculating ventricular function, yielding accurate measurements.

SUMMARY OF THE INVENTION

In one embodiment, the invention relates to a method of measuring ventricular function in an isolated, perfused heart using an intraventricular balloon connected to a plumbing circuit containing a fluid, the plumbing circuit including (a) a valve for selectively opening the plumbing circuit to (i) atmospheric pressure or (ii) a pressure control circuit of a pressure control apparatus or (b) a pressure control apparatus which can be selectively connected to the plumbing circuit, including the steps of establishing a base pressure by (1) opening the valve to atmospheric pressure or the pressure control circuit or (2) operating the pressure control apparatus, after equalization of the pressure within the intraventricular balloon with the base pressure, closing the valve or stopping operation of the pressure control apparatus, following the closing of the valve, measuring ventricular function as a function of a titrated infusion of fluid into the plumbing circuit and intraventricular balloon, performing an intervention, and repeating at least the first three steps.

In another embodiment, the invention relates to a system for measuring ventricular function in an isolated, perfused heart, including an intraventricular balloon adapted to be inserted into the isolated heart, a plumbing circuit containing a fluid, connected to the intraventricular balloon, a pressure transducer connected to the plumbing circuit, a pump, and a three-way valve connected to the plumbing circuit, the pump, and to the atmosphere, wherein opening the three-way valve to the atmosphere causes atmospheric pressure to be exerted by the intraventricular balloon on the isolated heart, and wherein subsequently opening the three-way valve to the pump causes the pressure exerted by the intraventricular balloon on the isolated heart to be equal to the sum of the atmospheric pressure and the pressure exerted by an infused volume of fluid.

DETAILED DESCRIPTION OF THE INVENTION

The following terms shall have, for the purposes of this application, the respective meanings set forth below.

Bioactive Agent: A bioactive agent is a substance such as a chemical that can act on a cell, virus, tissue, organ or organism, including but not limited to insecticides or drugs (i.e., pharmaceuticals) to create a change in the functioning of the cell, virus, organ or organism. Preferably, the organism is a mammal, more preferably a human or a mammal whose heart is traditionally used as model for human heart function.

Intervention: An intervention is any type of physical, physiological or pharmacological intervention in the function of a heart. Additions of bioactive agents to the fluid perfusing the heart is one example. Another example is surgical intervention to cause an ischemic event. Still another example is an alteration of nutrient or specific salt levels in the fluid perfused through the heart vasculature.

Figure 1:
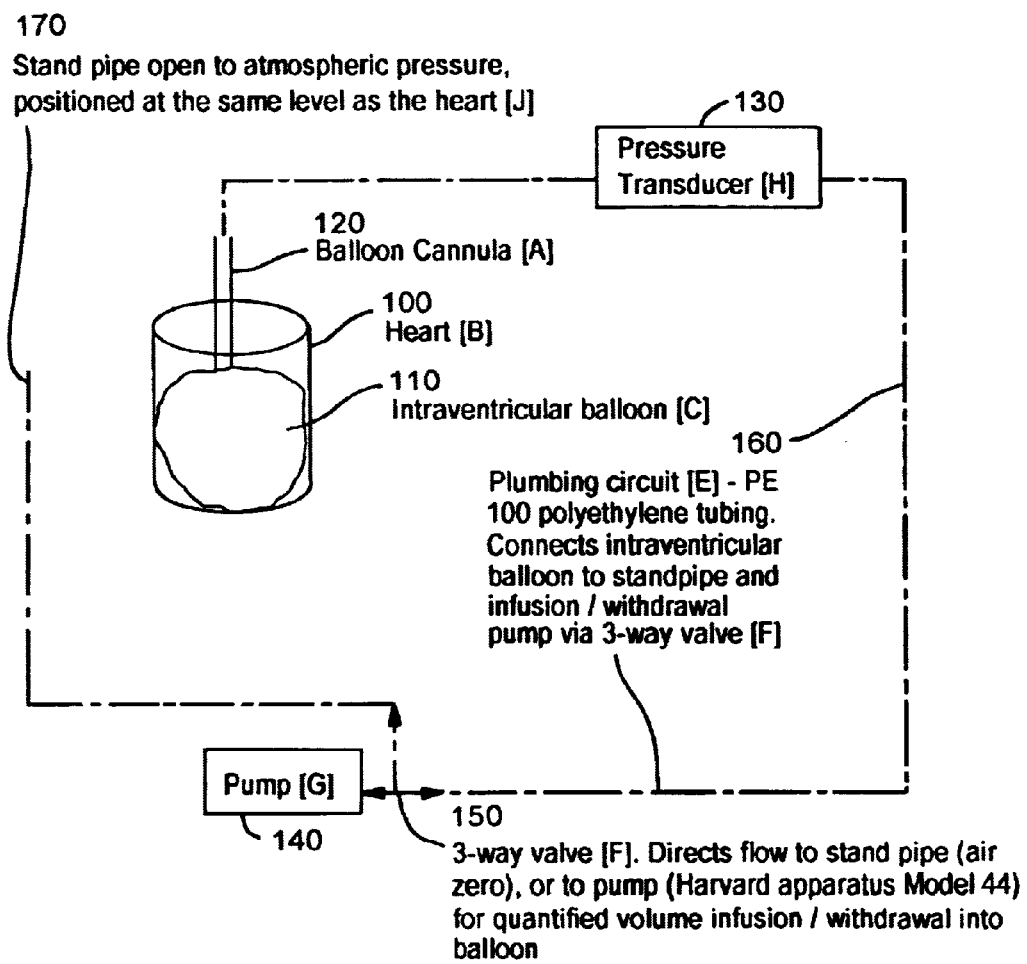
FIG. 1 illustrates a system in accordance with an embodiment of the present invention.

Referring to FIG. 1, isolated heart 100, which can be a rat, mouse, guinea pig, or other small mammal heart, is perfused with an oxygenated fluid (not shown). The oxygenated fluid can be an oxygenated (95% $O_2$, 5% $CO_2$, pH 7.4) Krebs-Henseleit solution comprised of 112 mM NaCl, 25 mM $NaHCO_3$, 5 mM KCl, 1 mM $KH_2PO_4$, 1.2 mM $MgSO_4$, 5.5 mM dextrose, and between 0.2 and 4.0 mM calcium. Intraventricular balloon 110, which can be a water-filled latex balloon fashioned for example from a latex finger cot (available from VWR Scientific of S. Plainfield, N.J. as part 55613-413), is attached to a cannula, such as a stainless steel cannula (of which model LL2 available from Hugo Sachs of March-Hugstetten, Germany is a suitable example). The cannula-balloon assembly is inserted into isolated heart 100 and connected to plumbing circuit 160, which can be comprised for example of polyethylene tubing. Plumbing circuit 160 is filled with a liquid, such as a saline solution. Pressure transducer 130, which can be model P23 available from Gould Instruments of Valley View, Ohio, is attached to plumbing circuit 160 and is used to measure intraventricular balloon pressure. Plumbing circuit 160 is also connected to three-way valve 150, which is also connected to pump 140 and stand pipe 170. Pump 140 can be for example a programmable infusion withdrawal pump, such as Harvard apparatus model 44 (Natick, Mass.).

Stand pipe 170 is open to atmospheric pressure and is positioned with its top preferably at the same height as isolated heart 100. The height is typically aligned with the top of the isolated heart. More importantly, even if there are inaccuracies in the alignment, the relative height is maintained through iterations of the method. The cross-section of the stand pipe is selected to be wide enough that variations in volume at the intraventricular balloon 110 provide only modest variations in column height, such as less than 0.5%. Other relative heights can be selected if they provide appropriate starting or base pressures for tests of ventricular function. A pressure other than atmospheric pressure can be utilized in an appropriate case as the base pressure, so long as such pressure is a constant pressure that can be repeatedly applied to plumbing circuit 160.

When three way valve 150 is open to stand pipe 170, atmospheric pressure is exerted on the fluid in plumbing circuit 160, which in turn exerts atmospheric pressure on intraventricular balloon 110 in isolated heart 100. When three way valve 150 is open to pump 140, it can be operated to force a volume of fluid into intraventricular balloon 110, thereby exerting a pressure on intraventricular balloon 110 different from atmospheric pressure.

Figure 2:
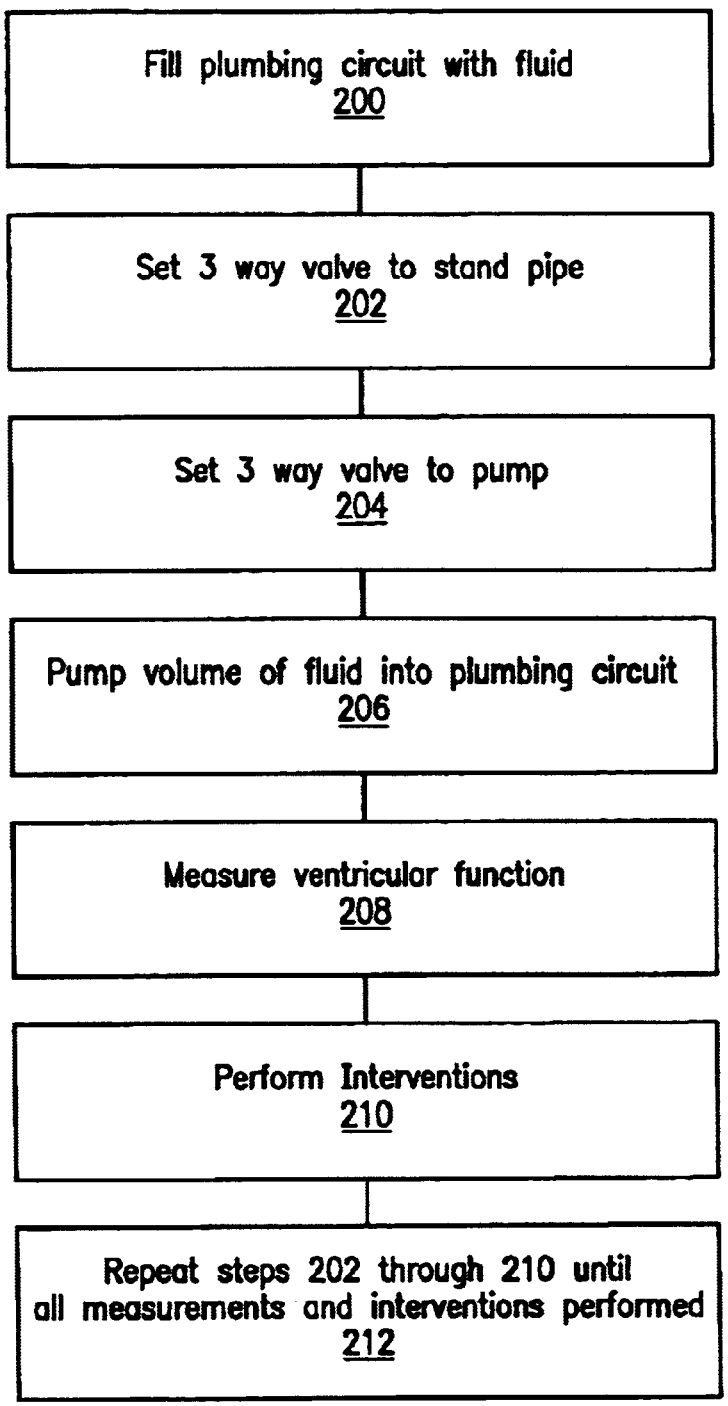
FIG. 2 illustrates a method in accordance with an embodiment of the present invention.

Referring to FIG. 2, a method in accordance with an embodiment of the present invention is illustrated. Prior to the performance of step 200, an intraventricular balloon is inserted into an isolated heart, such as a rat, mouse, or guinea pig heart, or the heart of another small mammal, and connected to a system such as the one illustrated in FIG. 1. Further details of one example are disclosed in exhibit A attached hereto. In step 200, plumbing circuit 160 is filled with a fluid. In an exemplary embodiment, the entire plumbing circuit is filled with a saline solution and all air in the plumbing circuit is flushed out.

In step 202, the three-way valve is set to direct the flow of fluid within the plumbing circuit to the stand pipe, thereby causing atmospheric pressure to be exerted on the intraventricular balloon. The beating of the isolated heart will in turn cause the intraventricular balloon to be resized so as to exert atmospheric pressure on the isolated heart. Typically the volume of the intraventricular balloon after resizing by the beating of the isolated heart will constitute between about 20% and about 40% of the volume of the left ventricle cavity. Optionally, the atmospheric pressure can be recorded at this time (either manually or using a pressure transducer) in order to allow verification of the lack of any meaningful changes in atmospheric pressure during the course of an experiment.

In other embodiments of the present invention, in lieu of utilizing a stand pipe to exert atmospheric pressure on the intraventricular balloon, a pump or other mechanism can be utilized to exert a fixed pressure on the intraventricular balloon. In this embodiment, any pump operable with the appropriate feedback to stably maintain an appropriate base or initial pressure for ventricular function measurements can be used. The pump can be, for example, a Harvard Apparatus Model 44 infusion/withdrawal Pump (available from Harvard Apparatus of South Natick, Mass.), a positive displacement pump (such as a piston, diaphragm pump or vane pump), a kinetic pump (such as a volute pump), or any other appropriate pump known in the art. Among positive displacement pumps, for the present purpose a single piston can operate to create pressure, with the displacement head sized to provide appropriate pressure responsiveness. The feedback can be provided by a pressure transducer fitted to measure pressure in the plumbing. Based on the pressure measurements, an operator can manually adjust the pump. Alternatively, the pressure transducer can send the pressure measurements to a controller operating the pump and appropriate adjustments can be made automatically. Methods known in the art can be used to control for pressure measurement oscillations from the transducer, such as integration, averaging of minima, maxima or transition points in the output values, or other noise reducing methods.

Such a pump and pressure feedback apparatus is referred to herein as a pressure control apparatus. Feedback can also be provided through measurements of delivered volume.

Preferably, the pressure control apparatus includes plumbing independent of the plumbing that extends to the intraventricular balloon, such that it can be constantly self adjusting to the base pressure. As with the use of atmospheric pressure, a valve preferably connects or disassociates the two systems. Preferably, the volume of the pressure control apparatus is high enough that connection to the first plumbing circuit does not create a marked change in the pressure of the pressure control apparatus. If there is a change on connection, the feedback control can be allowed time to re-establish the base pressure.

In step 204, the three way valve is set to direct the flow of fluid within the plumbing circuit to the pump. In step 206, a volume of fluid is pumped into the plumbing circuit by the pump, thereby increasing the pressure exerted on the isolated heart by the intraventricular balloon (if the volume of fluid pumped in is positive). In step 208, one or more measurements of ventricular function, such as contractile function, are made.

In step 210, an intervention is optionally performed. For example, a bioactive agent, such as isoproterenol, can be pumped into a nutrient fluid perfused through the isolated heart. Step 210 can be performed at any time prior to the performance of step 212, can be performed multiple times within one iteration of steps 202 through 210, and can be performed in multiple iterations of steps 202 through 210 (and can be performed only within selected iterations of steps 202 through 210). Although in some experiments, performing an intervention only after measurements of ventricular function at fixed, reproducible pressures have been performed is desirable, in other experiments interventions can be performed prior to measurements of ventricular function and even prior to the establishment of a fixed pressure.

In step 212, steps 202 through 210 are repeated until all desired measurements and interventions have been performed. By repeating step 202 following each intervention, changes in the size of the isolated heart caused by interventions are taken into account and measurements taken at a common infused volume prior to and following changes in the size of the heart caused by interventions are taken at a common pressure and are hence more meaningfully comparable. If step 202 is omitted following an intervention that changes the size of the isolated heart, measurements taken thereafter include distortions of a magnitude that can be difficult to determine and the measurements may be of reduced value.

In interpreting the results of the use of the present invention, the following equations are useful. First, the relationship between end-diastolic pressure and end-diastolic balloon volume is extremely well described by the following equation:

$$EDP = aV^2 + bV + c$$

where EDP is balloon end-diastolic pressure (mmHg), V is balloon volume ($\mu$l), and a, b, and c are curve fitting parameters. The positive root of this quadratic formula has the units of $\mu$l and yields the unloaded volume for any particular heart and balloon combination as defined by the following well known equation:

$$V = \frac{-b \pm \sqrt{b^2 - 4ac}}{2a}$$

Relative changes in ventricular end-diastolic volume can be obtained by comparing the positive root from serial EDP-balloon volume curves for the same heart and balloon combination for each intervention. The absolute shift in the unloaded ventricular volume for each heart can be expressed as the change ($\mu$l) relative to the control value.

Diastolic chamber stiffness (dP/dV) can be estimated, as explained in the attached exhibit A, as the slope of the best linear fit of the EDP-balloon volume data according to the following equation:

$$EDP = mV + b$$

where EDP is the end-diastolic pressure, V is the balloon volume, m is the chamber stiffness constant, and b is a curve fitting parameter. Linear fits where $r^2 \geq 0.95$ can be assured by restricting the stiffness data to infused balloon volumes between 40 and 100 $\mu$l. In order to accommodate physical differences in each balloon and heart combination, all stiffness values can be normalized, and expressed as a percent of their respective control values.

Prior to analysis, raw end-systolic pressures (0.5 $\mu$l balloon resolution) can be corrected for any balloon offset due to changes in ventricular diastolic volume according to the following equation:

$$ESP_c = ESP_{exp} - (EDP_{exp} - EDP_{ref})$$

where $ESP_c$ is the corrected end-systolic pressure, $ESP_{exp}$ is the raw experimental ESP, $EDP_{exp}$ is the raw experimental end-diastolic pressure, and $EDP_{ref}$ is the reference EDP (control). The corrected data can then be submitted for classic end-systolic pressure-volume relation (ESPVR) analysis. ESPVR can be assessed as the best linear fit of the end-systolic pressure and balloon volume data as described by the following equation:

$$ESP_c = mV + b$$

where $ESP_c$ is the corrected end-systolic pressure, V is the infused balloon volume, b is a curve fitting parameter, and m is the slope (end-systolic elastance; $F_{es}$).

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

That which is claimed is:

1. A method of measuring ventricular function in an isolated, perfused heart using an intraventricular balloon connected to a plumbing circuit containing a fluid, the plumbing circuit including (a) a valve for selectively opening the plumbing circuit to (i) atmospheric pressure or (ii) a pressure control circuit of a pressure control apparatus or (b) a pressure control apparatus which can be selectively connected to the plumbing circuit, comprising:

(a) to establish a base pressure, (1) opening the valve to atmospheric pressure or the pressure control circuit or (2) operating the pressure control apparatus;
 (b) after equalization of the pressure within the intraventricular balloon with the base pressure, closing the valve or stopping operation of the pressure control apparatus;
 (c) following the closing of the valve in step (b), measuring ventricular function as a function of a titrated infusion of fluid into the plumbing circuit and intraventricular balloon;
 (d) performing an intervention; and
 (e) repeating steps (a) through (c).

2. The method of claim 1, further comprising:
 (f) repeating step (d).

3. The method of claim 1, wherein the plumbing circuit includes a valve at a height aligned at a fixed height relative to the top of the heart for selectively opening the plumbing circuit to atmospheric pressure.

4. The method of claim 1, wherein the ventricular function measurements in step (c) are calculated based on a preload equal to the volume of fluid infused into the intraventricular balloon plus a constant.

5. The method of claim 4, wherein the constant is zero.

6. The method of claim 4, wherein the constant is the volume of the intraventricular balloon after the first iteration of step (b) and prior to the first iteration of step (c).

7. The method of claim 1, wherein the isolated heart is a rat heart.

8. The method of claim 1, wherein the isolated heart is a mouse heart.

9. The method of claim 1, wherein the isolated heart is a guinea pig heart.

10. The method of claim 1, wherein a three way valve is operated in steps (a) and (b).

11. The method of claim 1, wherein the intraventricular balloon is a latex balloon.

12. The method of claim 1, wherein the volume of the intraventricular balloon prior to the performance of step (c) is at least 20% of the volume of the left ventricle cavity prior to the insertion of the intraventricular balloon.

13. The method of claim 1, wherein the volume of the intraventricular balloon prior to the performance of step (c) is at less than 40% of the volume of the left ventricle cavity prior to the insertion of the intraventricular balloon.

14. The method of claim 1, wherein ventricular function is measured in step (c) using a pressure transducer connected to the plumbing circuit.

15. The method of claim 1, wherein the intervention comprises altering the concentration of or infusing a bioactive agent into a nutrient fluid perfused through the isolated heart.

16. The method of claim 1, wherein the intervention comprises altering the concentration of isoproterenol in a fluid flowing through the isolated heart.

17. A system for measuring ventricular function in an isolated, perfused heart, comprising:
 an intraventricular balloon adapted to be inserted into the isolated heart;
 a plumbing circuit containing a fluid, connected to said intraventricular balloon;
 a pressure transducer connected to said plumbing circuit;
 a pump; and
 a three-way valve connected to said plumbing circuit, said pump, and to the atmosphere,
 wherein opening said three-way valve to the atmosphere causes atmospheric pressure to be exerted by said intraventricular balloon on the isolated heart; and
 wherein subsequently opening said three-way valve to said pump causes the pressure exerted by said intraventricular balloon on the isolated heart to be equal to the sum of the atmospheric pressure and the pressure exerted by an infused volume of fluid.

* * * * *